United States Patent
Brandl et al.

(10) Patent No.: US 12,016,926 B2
(45) Date of Patent: Jun. 25, 2024

(54) TERPOLYMERS AND THEIR USE IN PHARMACEUTICAL DOSAGE FORMS

(71) Applicant: BASF SE, Ludwigshafen (DE)

(72) Inventors: Ferdinand Paul Brandl, Ludwigshafen (DE); Theo Smit, Ludwigshafen (DE); Felicitas Guth, Ludwigshafen (DE); Karl Kolter, Ludwigshafen (DE); Maximilian Angel, Kasendorf (DE); Frank Schmidt, Ludwigshafen (DE)

(73) Assignee: BASF SE (DE)

( * ) Notice: Subject to any disclaimer, the term of this patent is extended or adjusted under 35 U.S.C. 154(b) by 661 days.

(21) Appl. No.: 16/772,273

(22) PCT Filed: Dec. 7, 2018

(86) PCT No.: PCT/EP2018/083901
§ 371 (c)(1),
(2) Date: Jun. 12, 2020

(87) PCT Pub. No.: WO2019/121051
PCT Pub. Date: Jun. 27, 2019

(65) Prior Publication Data
US 2021/0069112 A1    Mar. 11, 2021

(30) Foreign Application Priority Data

Dec. 20, 2017   (EP) .................................... 17209070

(51) Int. Cl.
| | |
|---|---|
| A61K 9/16 | (2006.01) |
| A61K 31/216 | (2006.01) |
| A61K 31/5377 | (2006.01) |
| A61K 31/58 | (2006.01) |
| A61K 31/635 | (2006.01) |
| A61K 47/32 | (2006.01) |
| C08F 220/06 | (2006.01) |
| C08F 220/18 | (2006.01) |
| C08F 226/10 | (2006.01) |

(52) U.S. Cl.
CPC ............ *A61K 47/32* (2013.01); *A61K 9/1635* (2013.01); *A61K 31/216* (2013.01); *A61K 31/5377* (2013.01); *A61K 31/58* (2013.01); *A61K 31/635* (2013.01); *C08F 220/06* (2013.01); *C08F 220/1803* (2020.02); *C08F 220/1804* (2020.02); *C08F 220/1806* (2020.02); *C08F 226/10* (2013.01)

(58) Field of Classification Search
None
See application file for complete search history.

(56) References Cited

U.S. PATENT DOCUMENTS

| | | | |
|---|---|---|---|
| 3,810,977 A * | 5/1974 | Levine | C08F 218/08 424/47 |
| 5,196,188 A | 3/1993 | Potthoff-Karl et al. | |
| 7,282,218 B2 | 10/2007 | Kulkarni et al. | |
| 7,807,707 B2 * | 10/2010 | Bhogal | A61Q 5/02 424/70.22 |
| 7,858,076 B2 | 12/2010 | Nguyen-Kim et al. | |
| 2010/0137455 A1 | 6/2010 | Bouillo et al. | |
| 2014/0290148 A1 | 10/2014 | Huang | |

FOREIGN PATENT DOCUMENTS

| | | |
|---|---|---|
| CN | 1878540 A | 12/2006 |
| CN | 1890278 A | 1/2007 |
| JP | 2871276 B2 | 3/1999 |
| JP | 6348315 B2 | 6/2018 |
| WO | WO-2005/058383 A2 | 6/2005 |
| WO | WO-2014/159748 A1 | 10/2014 |
| WO | WO-2014/182710 A1 | 11/2014 |
| WO | WO-2014/182713 A1 | 11/2014 |
| WO | WO-2017/032650 A1 | 3/2017 |

OTHER PUBLICATIONS

Baghel et al., Polymeric Amorphous Solid Dispersions: A Review of Amorphization, Crystallization, Stabilization, Solid-State Characterization, and Aqueous Solubilization of Biopharmaceutical Classification System Class II Drugs, J. Pharm. Sci., 105(9):2527-44 (2016).

Brouwers et al., Supersaturating Drug Delivery Systems: The Answer to Solubility-Limited Oral Bioavailability?, J. Pharm. Sci., 98(8):2549-72 (2009).

Chiou et al., Pharmaceutical Applications of Solid Dispersion Systems, J. Pharm. Sci., 60(9):1281-302 (1971).

International Application No. PCT/EP2018/083901, International Search Report and Written Opinion, dated Feb. 11, 2019.

Warren et al., Using Polymeric Precipitation Inhibitors to Improve the Absorption of Poorly Water-Soluble Drugs: A Mechanistic Basis for Utility, J. Drug Target, 18(10):704-31 (2010).

Illescas, et al., "Synthesis and optical characterization of photoactive poly(2?phenoxyethyl acrylate) copolymers containing azobenzene units, prepared by frontal polymerization using novel ionic liquids as initiators", Journal of Polymer Science Part A: Polymer Chemistry, vol. 50, Issue 4, Nov. 28, 2011, pp. 821-830.

(Continued)

*Primary Examiner* — Tigabu Kassa
(74) *Attorney, Agent, or Firm* — Faegre Drinker Biddle & Reath LLP

(57) ABSTRACT

Terpolymer, wherein 20 to 35% by weight of the structural units are derived from acrylic acid, 45 to 60% by weight of the structural units from a hydrophobic methacrylate selected from a group consisting of isopropyl methacrylate, tert-butyl methacrylate and cyclohexyl methacrylate and 15 to 40% by weight of the structural units from a third olefinic monomer selected from the group consisting of N-vinyl lactam, hydroxy ethyl methacrylate and phenoxyethyl acrylate with the proviso that the total amount of structural units derived from the three monomer groups adds up to 100% by weight, and the use of the terpolymers as crystallization inhibitors in pharmaceutical dosage forms for inhibiting the recrystallization in an aqueous environment of a human or animal body of an active ingredient.

15 Claims, No Drawings

(56) References Cited

OTHER PUBLICATIONS

Meeussen, et al., "Phase behaviour of poly(N-vinyl caprolactam) in water", Polymer, vol. 41, Issue 24, Nov. 2000, pp. 8597-8602.

* cited by examiner

TERPOLYMERS AND THEIR USE IN PHARMACEUTICAL DOSAGE FORMS

CROSS-REFERENCE TO RELATED APPLICATIONS

This is the U.S. national phase of International Application No. PCT/EP2018/083901, filed Dec. 7, 2018, which claims the benefit of European Patent Application No. 17209070.6, filed on Dec. 20, 2017.

The present invention relates to novel terpolymers based on acrylic acid, a hydrophobic methacrylate and a third olefinic monomer, their use as pharmaceutical excipients for improving gastrointestinal adsorption, the respective pharmaceutical dosage forms and methods for making the terpolymers.

The intestinal absorption of poorly water-soluble drugs (BCS class II and IV) is limited by the maximum achievable concentration in the gastrointestinal lumen. Therefore, various approaches in formulation development aim at increasing the dissolution rate and improving drug solubility in the gastrointestinal tract. Administering the drug as a solution is a common approach to enhance the intestinal absorption of poorly water-soluble drugs. To this end, hydrophobic drugs are formulated using a mixture of co-solvents, surfactants, complexing agents (e.g., cyclodextrins) and/or oils. After oral administration, these formulations increase the total concentration of the drug that is present in solution; however, this approach does not necessarily result in an improved bioavailability. Depending on the lipophilicity of the drug, a large fraction of drug molecules is solubilized in a mixture of colloidal species (e.g., emulsified oil, micelles etc.). This fraction is unavailable for absorption, since only the free molecular species of the drug can permeate across the intestinal barrier. Furthermore, dilution and dispersion of the formulation in the gastrointestinal tract decreases the solubilization capacity. As a result, a metastable supersaturated state is generated that eventually leads to drug precipitation.

Besides the administration in solution, a number of formulation strategies exist that enable the delivery of poorly water-soluble drugs in a solid form. These approaches aim at generating high-energy or rapidly dissolving forms of the drugs (e.g., by milling, co-grinding, solvent evaporation, melting or crystal engineering) that induce supersaturation in the gastrointestinal tract. For example, in combination with suitable polymers (e.g., polyvinylpyrrolidone, vinylpyrrolidone-vinyl acetate copolymer, polyethylene glycol, polymethacrylates, cellulose derivatives etc.) and/or surfactants, poorly water-soluble drugs can be manufactured into solid dispersions (e.g., by spray drying or hot melt extrusion). These contain amorphous drug particles embedded in a polymer matrix that stabilizes the amorphous state by vitrification, specific drug-polymer interactions and/or reduced mobility. The release of the embedded drug molecules often depends on the dissolution rate of the polymer matrix. After dissolution of the dosage form in the gastrointestinal tract, the concentration of the drug in solution will be above the saturation solubility. This supersaturated state is thermodynamically unstable and the system tends to return to the equilibrium state by drug precipitation.

To benefit from the increased concentration, it is necessary to stabilize the supersaturated state in the gastrointestinal lumen for a time period sufficient for absorption. For example, cellulose derivatives (e.g., HPMC or HPMCAS) and vinyl polymers (e.g., polyvinyl alcohol, polyvinylpyrrolidone or vinylpyrrolidone-vinyl acetate copolymer) have been described to inhibit drug precipitation by interfering with nucleation and/or crystal growth. It is important to note that this type of stabilization is different from the stabilization of the amorphous state in the dosage form prior to application.

WO2014/159748 mentions the use of acrylate based crystallization-inhibiting agents, preferably a copolymer of butyl methacrylate, 2-dimethylaminoethyl methacrylate and methyl methacrylate in a weight ratio of 1:2:1.

WO 2005/058383 describes adhesive implants for parietal repair comprising water-soluble biocompatible polymers having adhesive properties which are copolymers based on alkyl acrylates such as octyl acrylates as well as acrylic acid and hydroxyalkyl (meth)acrylates.

WO 2014/182713 relates to statistical copolymers made from at least three different acrylate monomers such as alkyl(meth)acrylate, carbalkoxyalkyl (meth)acrylates, hydroxyalkyl (meth)acrylates and alkyl acetyl acrylates and their use for inhibiting drug crystallization and supersaturation maintenance. WO 2014/182710 refers to similar copolymers further substituted with sugar moieties. These copolymers show several disadvantages. First of all, not all of the monomer groups are readily available and need to be specifically synthesized. Another problem is that the copolymers have rather low glass transition temperatures which makes spray drying difficult. Lower glass transition temperatures are also disadvantageous with regard to storage stability because the dosage forms tend to the so-called "cold flow". Also, sugar substituted copolymers show instabilities when processed by melt-extrusion.

According to the prior art, cellulose derivatives such as HPMCAS are often considered the excipient of choice to inhibit drug precipitation [J. Brouwers, M. E. Brewster, P. Augustijns, Supersaturating drug delivery systems: The answer to solubility-limited oral bioavailability? Journal of Pharmaceutical Sciences, 98 (2008) 2549-2572; D. B. Warren, H. Benameur, C. J. H. Porter, C. W. Pouton, Using polymeric precipitation inhibitors to improve the absorption of poorly water-soluble drugs: A mechanistic basis for utility, Journal of Drug Targeting, 18 (2010) 704-731; S. Baghel, H. Cathcart, N. J. O'Reilly, Polymeric amorphous solid dispersions: A review of amorphization, crystallization, stabilization, solid-state characterization, and aqueous solubilization of biopharmaceutical classification system class II drugs, Journal of Pharmaceutical Sciences, 105 (2016) 2527-2544]. However, the effectiveness of HPMCAS and other known polymers is often not ideal, since these polymers have originally been optimized for other applications (e.g., coatings or thickening agents). So far, there are no excipients available that fulfill all requirements regarding variability, long-term stability, processability and performance.

The problem to be solved by the present invention was to develop excipients for pharmaceutical formulations that allow for a safe and efficient stabilization against recrystallization and precipitation from the supersaturated state after in vivo release of sparingly water-soluble active ingredients in the aqueous environment of the human or animal body in order to assure satisfactory bioavailability.

The problem was solved by finding terpolymers wherein i) 20 to 35% by weight of the structural units are derived from acrylic acid, ii) 45 to 60% by weight of the structural units from a hydrophobic methacrylate and iii) 15 to 40% by weight of the structural units from a third olefinic monomer selected from the group consisting of N-vinyl lactams, hydroxyethyl methacrylate and phenoxyethyl acrylate, with the proviso that the total amount of i), ii) and iii) corresponds to 100% by weight.

According to a preferred embodiment, the invention relates to terpolymers wherein i) 20 to 35% by weight of the structural units are derived from acrylic acid, ii) 45 to 60% by weight of the structural units from a hydrophobic methacrylate and iii) 15 to 40% by weight of the structural units from a third olefinic monomer selected from the group consisting of N-vinyl lactams, hydroxyethyl methacrylate and phenoxyethyl acrylate, with the proviso that the total amount of i), ii) and iii) corresponds to 100% by weight, and wherein the solubility in phosphate buffer of a pH of 6.8 under standard conditions is such, that the content of insoluble substances remaining on a membrane filter having an average pore size of 8 μm when a 0.3% by weight aqueous preparation of the terpolymer is filtered with the filter, is not higher than 25% by weight of the amount of terpolymer in the aqueous preparation.

The invention further relates to a process for making the inventive terpolymers by free-radically initiated polymerization of a monomer mixture of three different monomers to give a terpolymer.

In all inventive embodiments, acrylic acid can be submitted to polymerization either in the form of the free acid or as sodium or potassium acrylate (calculated as acrylic acid) or mixtures thereof.

The N-vinyl lactams can be N-vinylpyrrolidone or N-vinyl caprolactam, preferably N-vinylpyrrolidone, most preferably N-vinyl caprolactam.

Another aspect of the invention is the use of the terpolymers for inhibiting in vivo recrystallization of an active ingredient after release from a dosage form into the aqueous environment of the human or animal body and the respective dosage forms comprising the terpolymer and an active ingredient, wherein the active ingredient has a solubility in water under standard conditions of less than 0.1% by weight. Preferably, the solubility of the active ingredient in water under standard conditions is less than 0.05% by weight, the active ingredient being present in such dosage form in an amorphous state or molecularly dispersed. Amorphous means that less than 5% by weight are crystalline. The crystalline proportion can be measured by X-Ray diffraction methods.

In accordance with the present invention solubility whether in water, phosphate buffer or other suitable biologically relevant systems is always the solubility at standard conditions, i.e., a temperature of 23° C. and a pressure of 0.101325 MPa.

The solubility in phosphate buffer of a pH of 6.8 is carried under standard conditions by preparing an aqueous preparation of the terpolymer in water. The content of insoluble substances remaining on a membrane filter having an average pore size of 8 μm when a 0.3% by weight aqueous preparation of the terpolymer is filtered with the filter, is not higher than 25% by weight of the amount of terpolymer in the aqueous preparation. The membrane filter preferably is a polycarbonate filter membrane. Such membranes are commercially available. Preferably the residue is less than 10% by weight According to the invention, active ingredients sparingly soluble in water are those having a solubility of less than 0.1% by weight in water at standard conditions.

As already mentioned, suitable terpolymers for water-soluble formulations of active ingredients sparingly soluble in water, are those terpolymers having a solubility in phosphate buffer at a pH of 6.8 as defined above which are obtained by free-radically initiated polymerization of a monomer mixture of three different monomers to give a terpolymer wherein i) 20 to 35% by weight of the structural units are derived from acrylic acid, ii) 45 to 60% by weight of the structural units from a hydrophobic methacrylate and iii) 15 to 40% by weight of the structural units from the third olefinic monomer selected from the group consisting of N-vinyl lactams, hydroxyethyl methacrylate and phenoxyethyl acrylate, with the proviso that the total amount of i), ii) and iii) corresponds to 100% by weight, wherein the sparingly water-soluble active ingredient has a solubility of less than 0.1% by weight in water, artificial intestinal juice or gastric juice. The N-vinyl lactams can be N-vinylpyrrolidone or N-vinyl caprolactam, preferably N-vinylpyrrolidone, most preferably N-vinyl caprolactam.

Preference is given to polymers having a solubility in phosphate buffer at a pH of 6.8 as defined above and which are obtained by free-radically initiated polymerization of a monomer mixture of three different monomers to give a terpolymer wherein i) 20 to 35% by weight of the structural units are derived from acrylic acid, ii) 45 to 55% by weight of the structural units from a hydrophobic methacrylate selected from a group consisting of isopropyl methacrylate, tert-butyl methacrylate and cyclohexyl methacrylate and iii) 20 to 35% by weight of the structural units from the third olefinic monomer selected from the group consisting of N-vinyl lactams, hydroxyethyl methacrylate and phenoxyethyl acrylate, with the proviso that the total amount of i), ii) and iii) corresponds to 100% by weight. The N-vinyl lactams can be N-vinylpyrrolidone or N-vinyl caprolactam, preferably N-vinylpyrrolidone, most preferably N-vinyl caprolactam.

In all embodiments of the invention the amounts for the monomer derived moieties given in percent by weight are meant to include a deviation of ±1% by weight.

The polymers can be prepared in a conventional manner per se by free-radical polymerization. The polymerization is preferably carried out as a solution polymerization in organic solvents, preferably in alcohols such as methanol or ethanol, particularly in isopropanol. Such methods are known per se to those skilled in the art. Suitable initiators are, for example, organic peroxides such as diisobutyryl peroxide, 1,1,3,3-tetramethylbutyl peroxyneodecanoate, tert-amyl peroxyneodecanoate, tert-butyl peroxyneodecanoate, tert-butyl peroxyneoheptanoate, tert-butyl peroxypivalate, tert-butyl peroxy-2-ethylhexanoate and di-tert-butyl peroxide. Preferred are tert-butyl peroxypivalate, tert-butyl peroxy-2-ethylhexanoate and tert-butyl peroxyneodecanoate. Alternatively, alcohol-soluble azo initiators, particularly those azo starters which do not form physiologically critical side products such as dimethyl 2,2'-azobis(2-methylpropionate), can be used to initiate the polymerization.

The polymerization may be conducted at temperatures from 20 to 150° C., preferably 50 to 130° C. The polymerization can be carried out both under atmospheric pressure or in a closed reactor under elevated pressure. In this case it is possible to polymerize either under the pressure set up during the reaction, or the pressure can be adjusted by injecting a gas or evacuating.

It is also possible to carry out the polymerization in the presence of chain transfer agents, for example ethylhexyl thioglycolate.

The polymerization can be carried out continuously, semi-batch or as a batch process, the polymers preferably being obtained via a feed process.

The polymers are typically partly neutralized with aqueous alkaline solutions after the polymerization process. The degree of neutralization is adjusted in such a way that the pH of an aqueous solution of the partly neutralized terpolymer lies in the range of 5 to 9. Suitable aqueous alkaline solutions are sodium hydroxide or potassium hydroxide solutions.

The conversion of the polymer solutions into the solid form may be carried out by conventional drying processes such as spray-drying, freeze-drying or roller drying.

According to a preferred embodiment, the organic solvent is removed by water-vapor distillation to give aqueous solutions of the polymer which can subsequently be spray-dried to the respective powders.

According to another preferred embodiment, the organic reaction solution of the polymers is directly processed with active ingredients to give solid dispersions.

The weight average molecular weight of the terpolymers measured by gel permeation chromatography lies in the range of 7,000 to 100,000 g/mol, preferably 7,000 to 70,000 g/mol and most preferably 10,000 to 50,000 g/mol.

The glass transition temperatures calculated according to the Fox equation are in the range of >80° C., preferably higher than 100° C. and up to 150° C.:

$$\frac{1}{T_G} = \sum_i^n x_i \frac{1}{T_{G,i}}$$

$x_i$=mass fraction of the comonomer in the polymer
$T_{G,i}$=glass transition temperature of the homopolymer of the corresponding comonomer
$T_G$=glass transition temperature of the copolymer The glass transition temperatures may also be measured by differential scanning calorimetry at a heating rate of 20 K/min. The measurements can be performed according to DIN EN ISO 11357-2

The active ingredients can be selected from the group of pharmaceutical, nutritional or agrochemical actives.

Examples which may be mentioned here include antihypertensives, vitamins, cytostatics, especially taxol, anesthetics, neuroleptics, antidepressants, antibiotics, antimycotics, fungicides, chemotherapeutics, urologics, platelet aggregation inhibitors, sulfonamides, spasmolytics, hormones, immunoglobulins, sera, thyroid therapeutics, psychopharmaceuticals, Parkinson's drugs and other antihyperkinetics, ophthalmics, neuropathy preparations, calcium metabolism regulators, muscle relaxants, narcotics, antilipemics, liver therapeutics, coronary drugs, cardiac drugs, immunotherapeutics, regulatory peptides and their inhibitors, hypnotics, sedatives, gynecological drugs, gout remedies, fibrinolytics, enzyme preparations and transport proteins, enzyme inhibitors, emetics, weight-loss drugs, perfusion promoters, diuretics, diagnostics, corticoids, cholinergics, biliary therapeutics, antiasthmatics, broncholytics, beta-receptor blockers, calcium antagonists, ACE inhibitors, arteriosclerosis remedies, antiphlogistics, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists or antiviral active ingredients or active ingredients for the treatment of HIV infections and AID syndrome.

Preference is given to using the inventive terpolymers for preparing formulations with active ingredients sparingly soluble in water.

The formulations can be either real solutions in which both the active ingredient and the inventive terpolymer are dissolved in a suitable solvent or mixture of solvents, or solid dispersions in which the active ingredient is embedded in the solid polymer matrix in amorphous form. Solid dispersions are dispersions of one or more active ingredients in a solid polymer matrix [W. L. Chiou, S. Riegelman, Pharmaceutical applications of solid dispersion systems, Journal of Pharmaceutical Sciences, 60 (1971) 1281-1302]. Solid dispersions can be prepared by heating a physical mixture of the active ingredient and the polymer until it melts, followed by cooling and solidification (melting method). Alternatively, solid dispersions can be prepared by dissolving a physical mixture of the active ingredient and the polymer in a common solvent, followed by evaporation of the solvent (solvent method). Solid dispersions may contain the active ingredient molecularly dispersed in a crystalline matrix. Alternatively, solid dispersions may consist of an amorphous carrier; the active ingredient can be either molecularly dispersed in the carrier or form an amorphous precipitate. In any case, the active ingredient needs to be in an amorphous form. "Amorphous" means that less than 5% by weight of the active ingredient are crystalline.

According to one embodiment of the invention, the solid dispersions according to the invention can be prepared by means of the solvent method. The active ingredient and the polymer are dissolved in organic solvents or solvent mixtures and the solution is then dried. The dissolution can also take place at elevated temperatures (30-150° C.) and under pressure.

Suitable organic solvents are dimethylformamide, methanol or mixtures thereof, and mixtures with tetrahydrofuran. Suitable organic solvents also include ethanol, isopropanol, dimethylacetamide, acetone and/or dioxane. These solvents or solvent mixtures may additionally contain up to 20% by weight of water.

In principle, all types of drying are possible, such as, spray-drying, fluidized-bed drying, drum drying, freeze-drying, vacuum drying, belt drying, roller drying, carrier-gas drying, evaporation etc.

According to another embodiment of the invention, the solid dispersions are prepared by melt processes. The active ingredient is mixed with the polymer. By heating to temperatures of 50-180° C., the production of the solid dispersion takes place. Here, temperatures above the glass transition temperature of the polymer or the melting point of the active ingredient are advantageous. By adding a softening auxiliary, such as, for example, water, organic solvent, customary organic softeners, it is possible to correspondingly reduce the processing temperature. Of particular advantage are auxiliaries which can afterwards be very easily evaporated off again, i.e., having a boiling point below 180° C., preferably below 150° C.

According to a preferred embodiment, this type of preparation is carried out in a screw extruder. Which process parameters must be individually adjusted here can be determined by those skilled in the art by simple experiments in the scope of his or her conventional specialist knowledge.

According to a preferred embodiment, softeners are added during the melting. Preferred softeners are citric esters such as triethyl citrate or acetyl tributyl citrate, glycol derivatives such as polyethylene glycol, propylene glycol or poloxamers; castor oil and mineral oil derivatives; sebacate esters such as dibutyl sebacate), triacetin, fatty esters such as glycerol monostearate, fatty alcohols such as stearyl alcohol, fatty acids such as stearic acid, ethoxylated oils, ethoxylated fatty acids, ethoxylated fatty alcohols or vitamin E TPGS (tocopherol polyethylene glycol succinate). The softeners may be used in amounts of 0.1 to 40% by weight, preferably 1 to 20% by weight, based on the polymer.

The solid dispersions generated are amorphous. The amorphous state can be established by X-ray diffraction. The so-called "X-ray amorphous" state of the solid dispersions signifies that the crystalline proportion is less than 5% by weight.

The amorphous state can also by investigated with the aid of a DSC thermogram (Differential Scanning calorimetry). The solid dispersions according to the invention have no melting peaks but only a glass transition temperature, which depends also on the type of active ingredient used in the solid dispersions according to the invention. The glass transition temperatures are measured at a heating rate of 20 K/min.

In the course of preparation of the dosage forms according to the invention, customary pharmaceutical auxiliaries may optionally be processed at the same time. These are selected from the class of adsorbents, binders, disintegrants, dyes, fillers, flavorings or sweeteners, glidants, lubricants, preservatives, softeners, solubilizers, solvents or co-solvents, stabilizers (e.g., antioxidants), surfactants, or wetting agents.

The novel terpolymers allow for inhibiting the recrystallization of active pharmaceutical ingredients in the aqueous media of the gastrointestinal tract after release of the active ingredient from the dosage form in which the active ingredient was present in the form of an amorphous solid dispersion of the active ingredient in the polymer matrix of the novel terpolymers or in the form of a liquid solution of the active ingredient and the inventive terpolymer in a suitable solvent vehicle system.

EXAMPLES

Abbreviations

VP: N-vinylpyrrolidone
HEMA: 2-hydroxyethyl methacrylate
POEA: phenoxyethyl acrylate
tBMA: tert-butyl methacrylate
CHMA: cyclohexyl methacrylate
IPMA: isopropyl methacrylate
VC: N-vinylcaprolactam
AA: acrylic acid GPC-Method Description Polymer molecular weights were determined by size exclusion chromatography (SEC) at 35° C., using: dimethylacetamide containing 1 wt % trifluoroacetic acid and 0.5 wt % lithium bromide as eluent, narrow molecular weight distribution poly(methyl methacrylate) standards (commercially available from PSS Polymer Standard Solutions GmbH with molecular weights in the range from M=800 to M=2,200,000) and a differential refractive index (DRI) detector from DRI Wyatt Optilab DSP.

Solubility in Phosphate Buffer: Description of Test Method 300 mg of dried polymer was added to 100 mL phosphate buffer (pH 6.8) in a 150 mL glass screw cap bottle. The mixture was stirred at 300 rpm for 15 minutes at 23° C., using a magnetic stirrer and a 3-5 cm long magnetic stirrer bar. The mixture was subsequently filtered over a dried and weighed polycarbonate filter with a diameter of 47 mm and an average pore size of 8 μm (available from Whatman). The filter with the residue was dried overnight at 75° C. in a vacuum oven at 0.02 MPa. The amount of residue on the filter was determined by subtracting the weight of dried filter from the weight of dried filter containing the residue. The amount of residue is given as percentage of the total amount of polymer (300 mg).

The glass transition temperatures were calculated according to the Fox equation using the homopolymer Tg values given in Table 1.

$$\frac{1}{T_G} = \sum_i^n x_i \frac{1}{T_{G,i}}$$

$x_i$=mass fraction of the comonomer in the polymer
$T_{G,i}$=glass transition temperature of the homopolymer of the corresponding comonomer
$T_G$=glass transition temperature of the copolymer

TABLE 1

| Monomer | Homopolymer Tg (° C.) | Reference |
|---|---|---|
| N-Vinylpyrrolidone | 175 | a |
| 2-Hydroxyethyl methacrylate | 85 | a |
| Phenoxyethyl acrylate | 14 | b |
| tert-butyl methacrylate | 107 | a |
| Cyclohexyl methacrylate | 104 | a |
| Isopropyl methacrylate | 85 | a |
| N-Vinylcaprolactam | 145 | c |
| Acrylic acid | 106 | a |

[a]Glass transition temperatures of polymers, R. J. Andrews and E. A. Grulke, Polymer Hand-book, (4th Edition), 2003.
[b]J. Illescas, J. Polym. Sci. A, Polym. Chem 2012, 50, 821-830.
[c]F. Meeussen, Polymer 2000, 41, 8597-8602

Residual Monomer Amounts

VP, AA and VC contents were determined by reversed-phase liquid chromatography using UV detection at an absorbance wavelength of 235 nm for VP and of 205 nm for AA and VC. Quantification has been performed by external calibration. An aliquot of the sample was dissolved in methanol and was directly injected. Chromatographic separation was achieved by using gradient elution.

HEMA, tBMA, POEA, CHMA and IPMA contents were determined by the means of capillary gas chromatography using a flame ionization detector (FID). Quantification was performed by standard addition. An aliquot of the sample was dissolved in 2-propanol and injected on a non-polar capillary column coated with a stationary phase of dimethylpolysiloxane.

Polymer Synthesis

Polymer A1

A two-liter glass reactor, equipped with a mechanical stirrer, a condenser, a nitrogen sweep, a thermometer and inlets for the gradual additions of monomer and initiator, was charged with 240 grams isopropanol. A monomer solution was prepared by dissolving 75 grams of acrylic acid, 165 grams of tert-butyl methacrylate and 60 grams of N-vinylpyrrolidone in 266 grams isopropanol. An initiator solution was prepared by dissolving 3.84 grams tert-butyl peroxypivalate solution (75 wt % in mineral spirits) in 200 grams of isopropanol. A total of 10 wt % of the monomer solution was added to the reactor charge and the resulting solution was heated to 75° C. under stirring at 100 rpm. A total of 10 wt % of the initiator solution was subsequently added and the temperature was increased to 80° C. The remaining 90 wt % of the monomer and the initiator solutions were then added separately at constant feed rate to the stirring reactor charge over 4 and 5 hours respectively. During these additions, the temperature of the reaction mixture was maintained at 80° C. After the additions were complete, the reaction mixture was stirred at 80° C. for an additional hour and was then allowed to cool to ambient temperature. A sample was taken from the mixture and dried for SEC measurements. Another sample was taken for residual monomer content measurements. Approximately 150 ml water was added and the pH of the reaction mixture was subsequently set by the addition of a 25 wt % aqueous sodium hydroxide solution. Volatiles were removed and the product was dried overnight in a vacuum oven at 75° C. at 0.02 MPa.

Polymers B1 and C1 were prepared analog to Polymer A1.

Variations are given in Table 1.

TABLE 2

| Polymer | Third monomer | AA | tBMA | Third monomer | pH |
|---|---|---|---|---|---|
| A1 | VP | 75 (25.0) | 165 (56.2) | 60 (18.8) | 7.0 |
| B1 | HEMA | 75 (22.9) | 165 (56.5) | 60 (20.6) | 7.5 |
| C1 | POEA | 90 (28.4) | 150 (51.4) | 60 (20.2) | 6.9 |

Monomer amounts in synthesis in g. Number in brackets is the content of the monomer in the polymer in wt %. The pH refers to the pH of the polymer solution after the addition of aqueous sodium hydroxide solution.

Polymer A3

A two-liter glass reactor, equipped with a mechanical stirrer, a condenser, a nitrogen sweep, a thermometer and inlets for the gradual additions of monomer and initiator, was charged with a solution of 60 grams N-vinylpyrrolidone in 150 grams isopropanol. A monomer solution was prepared by dissolving 75 grams of acrylic acid and 165 grams of tert-butyl methacrylate in 152 grams isopropanol and an initiator solution was prepared by dissolving 4.0 grams tert-butyl peroxypivalate solution (75 wt % in mineral spirits) in 150 grams of isopropanol. A total of 10 wt % of the monomer solution was added to the reactor charge and the resulting solution was heated to 70° C. under stirring at 100 rpm. A total of 10 wt % of the initiator solution was subsequently added and the temperature was increased to 75° C. The remaining 90 wt % of the monomer and the initiator solutions were then added separately at constant feed rate to the stirring reactor charge over 4 and 6 hours respectively. During these additions, the temperature of the reaction mixture was maintained at 75° C. After the additions were complete, the reaction mixture was stirred at 75° C. for an additional hour and was then allowed to cool to ambient temperature. A sample was taken from the mixture and dried for SEC measurements. Another sample was taken for residual monomer content measurements. Approximately 150 ml water was added and the pH of the reaction mixture was subsequently set by the addition of a 25 wt % aqueous sodium hydroxide solution. The pH of the reaction mixture was set by the addition of a 25 wt % aqueous sodium hydroxide solution. Volatiles were removed under reduced pressure and the product was dried overnight in a vacuum oven at 75° C. at 0.02 MPa.

Polymers A2 and A4 to A8 were prepared analog to Polymer A3. Polymer A8 was prepared using 4.0 g of dimethyl 2,2'-azobis(2-methylpropionate) instead of 4.0 grams tert-butyl peroxypivalate solution. Variations are given in Table 3.

TABLE 3

| Polymer | VP | AA | tBMA | pH |
|---|---|---|---|---|
| A2 | 60 (20.1) | 67.5 (22.2) | 172.5 (57.8) | 7.0 |
| A3 | 60 (20.1) | 75 (24.6) | 165 (55.3) | 7.9 |
| A4 | 60 (20.1) | 82.5 (27.0) | 157.5 (52.9) | 7.0 |
| A5 | 60 (20.2) | 90 (29.3) | 150 (50.5) | 6.9 |
| A6* | 60 (20.2) | 120 (39.4) | 120 (40.4) | 7.0 |
| A7 | 90 (30.1) | 67.5 (22.4) | 142.5 (47.5) | 7.0 |
| A8 | 60 (20.1) | 75 (24.6) | 165 (55.3) | 7.5 |

Monomer amounts in synthesis in g. Number in brackets is the content of the monomer in the polymer in wt %. The pH refers to the pH of the polymer solution after the addition of aqueous sodium hydroxide solution.

*For comparison

Polymers C2, C3, C4, D1, E1 and F1 were prepared analog to Polymer A3. Polymer C3 was prepared without VP in the pre-feeding charge and with 60 g of POEA included in the monomer feed. Polymer D1 was prepared with 165 g CHMA instead of 165 g tBMA in the monomer feed. Polymer E1 was prepared with 165 g IPMA instead of 165 g tBMA in the monomer feed. Polymer F1 was prepared using VC instead of VP. Like VP, VC was included in the pre-feeding charge. Polymer F1 was synthesized with 300 g instead of 150 g of isopropanol in the pre-feeding charge and with 255 g instead of 152 g of isopropanol in the monomer feed. Variations are summarized in Table 4.

TABLE 4

| Polymer | tBMA | CHMA | IPMA | VP | VC | AS | POEA | pH |
|---|---|---|---|---|---|---|---|---|
| C2 | 157.5 (53.1) | — | — | — | — | 82.5 (26.8) | 60 (20.1) | 7.1 |
| C3 | 150 (50.6) | — | — | — | — | 90 (29.3) | 60 (20.1) | 7.1 |
| C4 | 142.5 (48.1) | — | — | — | — | 97.5 (31.8) | 60 (20.1) | 7.0 |
| D1 | — | 165 (55.3) | — | 60 (20.2) | — | 75 (24.5) | — | 7.9 |
| E1 | — | — | 165 (55.6) | 60 (20.0) | — | 75 (24.4) | — | 6.9 |
| F1 | 135 (45.6) | — | — | — | 90 (30.4) | 75 (24.1) | — | 7.9 |

Monomer amounts in synthesis in g. Number in brackets is the content of the monomer in the polymer in wt %. The pH refers to the pH of the polymer solution after the addition of aqueous sodium hydroxide solution.

The amount of residue is given as percentage of the total amount of polymer used in the described solubility test. The results are listed in Table 5.

TABLE 5

| Polymer | Residue in solubility test (wt %) | Calculated Tg (° C.) | Mw |
|---|---|---|---|
| A1 | 2.5 | 118 | 20 700 |
| A2 | 79.0 | 118 | 40 400 |
| A3 | 0.2 | 119 | 38 900 |
| A4 | 0.3 | 119 | 36 600 |
| A5 | 0 | 119 | 34 700 |
| A6* | 0.3 | 119 | 26 300 |
| A7 | 0.4 | 125 | 42 000 |
| A8 | 0 | 119 | 30 700 |
| B1 | 9.1 | 102 | 25 400 |
| C1 | 2.5 | 83 | 14 500 |
| C2 | 12.3 | 84 | 27 300 |
| C3 | 0.7 | 84 | 25 100 |
| C4 | 0.4 | 83 | 24 900 |

TABLE 5-continued

| Polymer | Residue in solubility test (wt %) | Calculated Tg (° C.) | Mw |
|---|---|---|---|
| D1 | 0.8 | 117 | 27 200 |
| E1 | 0 | 105 | 38 200 |
| F1 | 0 | 117 | 23 000 |

*For comparison

Preparation of Amorphous Solid Dispersions Via Spray Drying

Celecoxib-Polymer Formulations (10 wt % Drug Loading):

The solid dispersions were composed of celecoxib and Polymer A7. To prepare the formulation, 3.0 g of celecoxib and 27.0 g of polymer were dissolved in 570 g of methanol (5 wt % solids content). Spray drying was performed on a Büchi Mini Spray Dryer B-290 equipped with a 0.7 mm two-fluid nozzle under the following conditions:

| | |
|---|---|
| Nitrogen flow rate | 35 m³/h |
| Inlet temperature | 85-105° C. |
| Outlet temperature | 50-70° C. |
| Atomizing pressure | 0.7 MPa |
| Liquid flow rate | 300 g/h |

The product was collected using a cyclone. The drug content of the spray-dried formulations was determined by measuring the UV absorbance at 252 nm; the solid-state properties were analyzed using powder X-ray diffraction (PXRD):

| | |
|---|---|
| Drug content (UV spectroscopy) | 10.3-10.7 wt % |
| Solid-state properties (PXRD) | X-ray amorphous |

Celecoxib-Polymer Formulations (25 wt % Drug Loading):

Solid dispersions were composed of celecoxib and Polymer A1, Polymer A2, Polymer A3, Polymer A4, Polymer A5, Polymer A6, Polymer A7, Polymer A8, Polymer B1, Polymer C1, Polymer C2, Polymer C3, Polymer C4, Polymer D1, Polymer E1, Polymer F1, HPMCAS-LF, HPMCAS-MF or HPMCAS-HF. To prepare the formulations, 2.5 g of celecoxib and 7.5 g of polymer were dissolved in 190 g of methanol or a 1:1 mixture of methanol and tetrahydrofuran (5 wt % solids content). Spray drying was performed on a Büchi Mini Spray Dryer B-290 equipped with a 0.7 mm two-fluid nozzle under the following conditions:

| | |
|---|---|
| Nitrogen flow rate | 35 m³/h |
| Inlet temperature | 85-105° C. |
| Outlet temperature | 50-70° C. |
| Atomizing pressure | 0.7 MPa |
| Liquid flow rate | 300 g/h |

The product was collected using a cyclone. The drug content of the spray-dried formulations was determined by measuring the UV absorbance at 252 nm; the solid-state properties were analyzed using powder X-ray diffraction (PXRD):

| | |
|---|---|
| Drug content (UV spectroscopy) | 24.2-27.6 wt % |
| Solid-state properties (PXRD) | X-ray amorphous |

Danazol-Polymer Formulations (10 wt % Drug Loading):

Solid dispersions were composed of danazol and Polymer A1, Polymer A2, Polymer A3, Polymer A4, Polymer A5, Polymer A6, Polymer A7, Polymer A8, Polymer B1, Polymer C1, Polymer C3, Polymer D1, Polymer E1, Polymer F1, HPMCAS-LF, HPMCAS-MF or HPMCAS-HF. To prepare the formulations, 1.5 g of danazol and 13.5 g of polymer were dissolved in 285 g of methanol or a 1:1 mixture of methanol and tetrahydrofuran (5 wt % solids content). Spray drying was performed on a Büchi Mini Spray Dryer B-290 equipped with a 0.7 mm two-fluid nozzle under the following conditions:

| | |
|---|---|
| Nitrogen flow rate | 35 m³/h |
| Inlet temperature | 85-105° C. |
| Outlet temperature | 50-70° C. |
| Atomizing pressure | 0.7 MPa |
| Liquid flow rate | 300 g/h |

The product was collected using a cyclone. The drug content of the spray-dried formulations was determined by measuring the UV absorbance at 286 nm; the solid-state properties were analyzed using powder X-ray diffraction (PXRD):

| | |
|---|---|
| Drug content (UV spectroscopy) | 9.4-11.7 wt % |
| Solid-state properties (PXRD) | X-ray amorphous |

In Vitro Release Experiments

Preparation of Phosphate Buffer pH 6.8

To prepare 5 L of phosphate buffer pH 6.8, 34.025 g of potassium dihydrogen phosphate was placed in a five-liter volumetric flask and dissolved in approximately 1 L of water. Then, 112 mL of a 1 M sodium hydroxide solution was added; the solution was diluted with water to 5 L. If necessary, the pH of the solution was adjusted to 6.8.

Dissolution Testing in Phosphate Buffer pH 6.8

In vitro dissolution tests were done to quantify the drug release and measure the maintenance of supersaturation. To this end, 100 mL of phosphate buffer pH 6.8 was filled into an Erlenmeyer flask and placed onto a multi-position magnetic stirrer (stirring speed approximately 300 rpm). After a temperature of 37° had been reached, a defined amount of the spray-dried formulation (equivalent to a drug concentration of 0.14 mg/ml) was added. Samples of 1000 µL were withdrawn after 5 min, 15 min, 30 min, 60 min, 90 min, 120 min, 180 min, 240 min, 300 min and 360 min. The samples were pipetted into microcentrifuge tubes and centrifuged for 3 min at 14,680 rpm to remove the precipitate. The clear supernatant was diluted with methanol (1:4 or 1:10, depending on the drug concentration); the concentration of the drug in solution was determined by UV spectroscopy using a calibration curve of the pure drug in methanol. To evaluate the performance of the polymer, the area under the concentration-time curve (AUC) was calculated as follows:

$$AUC_{0 \to t_n} = \frac{1}{2} \sum_{i=1}^{n-1} (C_{t_i} + C_{t_{i+1}}) \cdot (t_{i+1} - t_i)$$

$C_t$=Concentration at time t in mg/mL
t=Time in min

TABLE 6

AUC values of celecoxib and danazol after release from solid dispersions with Polymer A2, Polymer A3, Polymer A4, Polymer A5 and Polymer A6; drug release was tested in phosphate buffer pH 6.8.

| Polymer | Drug | Loading | Mean AUC ± SD (mg/mL min) |
|---|---|---|---|
| A2 | Celecoxib | 25.0% | 7.30 ± 0.06 |
| A3 | Celecoxib | 24.8% | 47.42 ± 5.33 |
| A4 | Celecoxib | 24.8% | 20.94 ± 2.15 |
| A5 | Celecoxib | 25.1% | 18.95 ± 0.69 |
| A6* | Celecoxib | 25.7% | 4.82 ± 0.21 |
| A7 | Celecoxib | 10.3% | 47.82 ± 1.13 |
| A7 | Celecoxib | 25.3% | 12.49 ± 0.94 |
| A8 | Celecoxib | 24.2% | 26.60 ± 1.59 |
| C2 | Celecoxib | 26.5% | 5.31 ± 0.15 |
| C3 | Celecoxib | 25.3% | 8.18 ± 0.30 |
| C4 | Celecoxib | 26.5% | 6.73 ± 0.20 |
| D1 | Celecoxib | 25.2% | 31.13 ± 1.55 |
| E1 | Celecoxib | 25.5% | 25.72 ± 4.41 |
| F1 | Celecoxib | 25.0% | 42.58 ± 2.13 |
| A2 | Danazol | 9.7% | 3.18 ± 0.27 |
| A3 | Danazol | 9.4% | 34.99 ± 6.43 |
| A4 | Danazol | 10.1% | 16.29 ± 1.43 |
| A5 | Danazol | 10.0% | 13.30 ± 1.47 |
| A6* | Danazol | 10.8 | 1.28 ± 0.28 |
| A7 | Danazol | 9.7% | 29.71 ± 3.88 |
| A8 | Danazol | 9.7% | 32.08 ± 0.54 |
| C2 | Danazol | 10.2% | 5.56 ± 0.46 |
| C3 | Danazol | 9.9% | 5.48 ± 0.69 |
| C4 | Danazol | 10.9% | 2.59 ± 0.16 |
| D1 | Danazol | 9.8% | 24.21 ± 1.97 |
| E1 | Danazol | 10.5% | 12.05 ± 3.05 |
| F1 | Danazol | 9.7% | 45.55 ± 1.10 |

*For comparison

TABLE 7

AUC values of celecoxib, danazol, fenofibrate and gefitinib after release from solid dispersions with Polymer A1, Polymer B1, Polymer C1, HPMCAS-HF, HPMCAS-MF and HPMCAS-LF; drug release was tested in 0.08M HCl and phosphate buffer pH 6.8 (pH-shift experiment).

| Polymer | Drug | Loading | Mean AUC ± SD (mg/mL min) |
|---|---|---|---|
| A1 | Celecoxib | 26.3% | 30.83 ± 1.25 |
| B1 | Celecoxib | 27.6% | 29.22 ± 1.88 |
| C1 | Celecoxib | 27.0% | 6.69 ± 0.41 |
| HMPCAS-HF | Celecoxib | 25.8% | 3.86 ± 0.18 |
| HPMCAS-MF | Celecoxib | 25.6% | 8.75 ± 0.48 |
| HPMCAS-LF | Celecoxib | 25.7% | 11.65 ± 0.73 |
| A1 | Danazol | 10.1% | 41.71 ± 3.69 |
| B1 | Danazol | 11.7% | 35.08 ± 2.31 |
| C1 | Danazol | 10.9% | 8.05 ± 0.58 |
| HMPCAS-HF | Danazol | 11.1% | 2.07 ± 0.20 |
| HPMCAS-MF | Danazol | 10.6% | 2.58 ± 0.75 |
| HPMCAS-LF | Danazol | 11.3% | 1.35 ± 0.23 |
| A1 | Fenofibrate | 9.8% | 12.42 ± 2.84 |
| B1 | Fenofibrate | 10.6% | 8.31 ± 1.35 |
| C1 | Fenofibrate | 9.6% | 12.22 ± 0.85 |
| HMPCAS-HF | Fenofibrate | 10.0% | 1.13 ± 0.36 |
| HPMCAS-MF | Fenofibrate | 10.7% | 0.87 ± 0.22 |
| HPMCAS-LF | Fenofibrate | 10.4% | 1.08 ± 0.26 |
| A1 | Gefitinib | 24.5% | 44.28 ± 1.71 |
| B1 | Gefitinib | 27.6% | 23.09 ± 1.63 |
| C1 | Gefitinib | 27.5% | 16.22 ± 0.55 |
| HMPCAS-HF | Gefitinib | 23.3% | 21.51 ± 0.72 |
| HPMCAS-MF | Gefitinib | 25.5% | 32.00 ± 1.09 |
| HPMCAS-LF | Gefitinib | 26.7% | 28.30 ± 1.35 |

The invention claimed is:

1. A pharmaceutical dosage form, comprising (a) a terpolymer, wherein 20 to 35% by weight of the structural units are derived from acrylic acid, 45 to 60% by weight of the structural units from a hydrophobic methacrylate selected from a group consisting of isopropyl methacrylate, tert-butyl methacrylate and cyclohexyl methacrylate and 15 to 40% by weight of the structural units from a third olefinic monomer selected from the group consisting of N-vinyl lactam, hydroxy ethyl methacrylate and phenoxyethyl acrylate with the proviso that a total amount of structural units derived from the three monomer groups adds up to 100% by weight and (b) an active pharmaceutical ingredient with a solubility in water at standard conditions of less than 0.1% by weight, wherein the active ingredient is present in an amorphous form, and
wherein the pharmaceutical dosage form is an oral pharmaceutical dosage form.

2. The pharmaceutical dosage form according to claim 1, wherein a solubility for the terpolymer in phosphate buffer of a pH of 6.8 under standard conditions is such that a content of insoluble substances remaining on a membrane filter having an average pore size of 8 µm when a 0.3% by weight aqueous preparation of the terpolymer is filtered with the filter, is not higher than 25% by weight of the amount of terpolymer in the aqueous preparation.

3. The pharmaceutical dosage form according to claim 1, wherein the hydrophobic methacrylate is tert-butyl methacrylate.

4. The pharmaceutical dosage form according to claim 1, wherein the N-vinyl lactam is N-vinyl pyrrolidone.

5. The pharmaceutical dosage form according to claim 1, wherein the N-vinyl lactam is N-vinyl caprolactam.

6. The pharmaceutical dosage form according to claim 1, wherein the terpolymer has a calculated glass transition temperature in a range of 80 to 150° C.

7. The pharmaceutical dosage form according to claim 1, wherein the terpolymer has a calculated glass transition temperature in the range of 100 to 150° C.

8. The pharmaceutical dosage form according to claim 1, wherein an amount of tert-butyl methacrylate derived structural units lies in a range of 45 to 55% by weight.

9. The pharmaceutical dosage form according to claim 1, wherein the amount of acrylic acid derived structural units lies in the range of 20 to 30% by weight.

10. The pharmaceutical dosage form according to claim 1, wherein the amount of structural units derived from the third olefinic monomer lies in the range of 20 to 35% by weight.

11. The pharmaceutical dosage form according to claim 1, wherein the terpolymer has a weight average molecular weight in the range of 7,000 to 100,000 g/mol.

12. The pharmaceutical dosage form according to claim 1, wherein the terpolymer is partly neutralized to provide a pH in the range of 5 to 9 upon dissolution in water.

13. The pharmaceutical dosage form of claim 1 in a form of a solid dispersion.

14. The pharmaceutical dosage of claim 13 wherein the active pharmaceutical ingredient is present in the solid dispersion at a loading of 9.4% to 27.5%, by weight, based on the weight of terpolymer (a) and active pharmaceutical ingredient (b).

15. A method of inhibiting recrystallization of an active ingredient in an aqueous environment of a human or animal comprising administering an oral dosage form comprising the active ingredient and a terpolymer of claim 1, wherein the active ingredient has a solubility in water at standard conditions of less than 0.1% by weight and is present in the pharmaceutical dosage form in an amorphous form.

* * * * *